(12) United States Patent  (10) Patent No.: US 8,585,743 B2
Ampuero et al.  (45) Date of Patent: Nov. 19, 2013

(54) LOW PROFILE SCREW AND WASHER SYSTEM FOR BONE PLATING

(75) Inventors: Eduardo A. Ampuero, Miami, FL (US); Alfredo Castaneda, Miami, FL (US); Jose Luis Francese, Miami Springs, FL (US); Juergen A. Kortenbach, Miami Springs, FL (US); Robert Sixto, Jr., Miami, FL (US)

(73) Assignee: Biomet C.V., Gibraltar (GI)

( * ) Notice: Subject to any disclaimer, the term of this patent is extended or adjusted under 35 U.S.C. 154(b) by 993 days.

(21) Appl. No.: 12/210,627

(22) Filed: Sep. 15, 2008

(65) Prior Publication Data

US 2010/0069969 A1 Mar. 18, 2010

(51) Int. Cl.
*A61B 17/84* (2006.01)

(52) U.S. Cl.
USPC .......................... 606/300; 606/301; 606/290

(58) Field of Classification Search
USPC ......... 411/147–150, 260–261, 270, 275, 330, 411/368–370, 371.2, 372, 540, 982–983, 411/531–53, 158, 160, 161, 396, 531–533, 411/546–548; 606/246–275, 300–321, 606/286–291; 16/2.1–2.5
See application file for complete search history.

(56) References Cited

U.S. PATENT DOCUMENTS

| | | | |
|---|---|---|---|
| 2,746,506 A * | 5/1956 | Poupitch | 411/134 |
| 4,793,757 A * | 12/1988 | Peterson | 411/533 |
| 5,562,663 A * | 10/1996 | Wisnewski et al. | 606/250 |
| 5,797,912 A | 8/1998 | Runciman et al. | |
| 6,030,389 A * | 2/2000 | Wagner et al. | 606/71 |
| 6,063,090 A * | 5/2000 | Schlapfer | 606/270 |
| 6,331,179 B1 | 12/2001 | Freid et al. | |
| 6,454,769 B2 | 9/2002 | Wagner et al. | |
| 6,730,093 B2 * | 5/2004 | Saint Martin | 606/303 |
| 6,955,677 B2 * | 10/2005 | Dahners | 606/287 |
| 6,964,664 B2 | 11/2005 | Freid et al. | |
| 2002/0133158 A1 * | 9/2002 | Saint Martin | 606/72 |
| 2004/0267261 A1 | 12/2004 | Derouet | |
| 2006/0217716 A1 * | 9/2006 | Baker et al. | 606/61 |
| 2007/0233125 A1 | 10/2007 | Wahl | |

FOREIGN PATENT DOCUMENTS

EP 0997107 A 5/2000
EP 1813216 A 8/2007

* cited by examiner

*Primary Examiner* — Matthew Lawson
(74) *Attorney, Agent, or Firm* — Gordon & Jacobson, PC

(57) ABSTRACT

A low profile bone screw system includes a retainable washer and a low profile bone screw having a smooth conical head for insertion into the washer. The washer has an axial bore with a conical portion for fully seating the screw head and a smooth outer surface shaped like the head of a conventional compression bone screw head. Washer dispensing units are also provided.

16 Claims, 5 Drawing Sheets

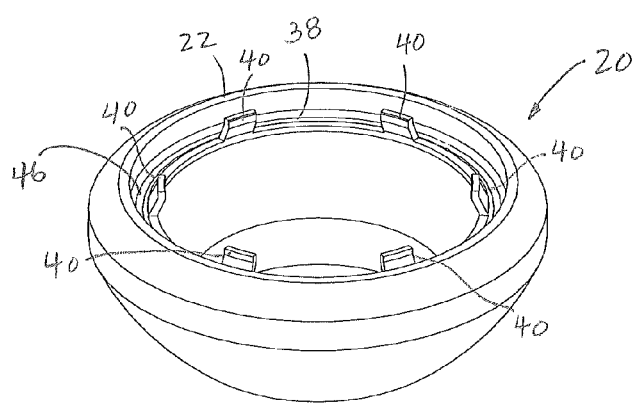
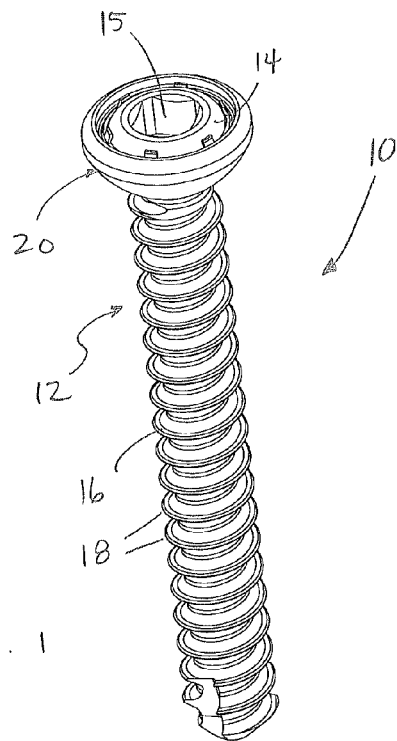
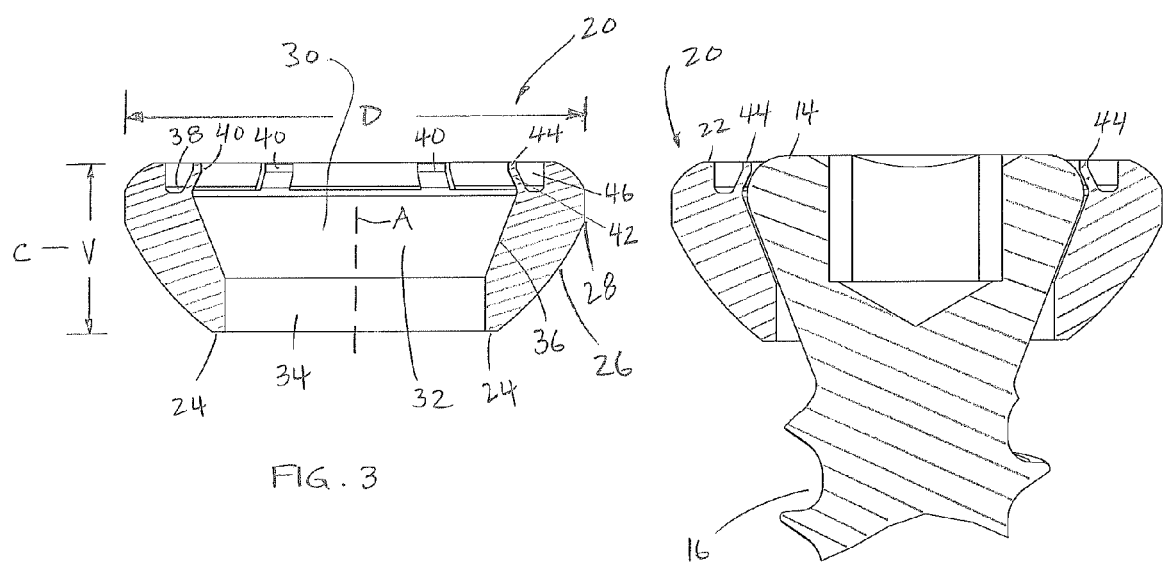
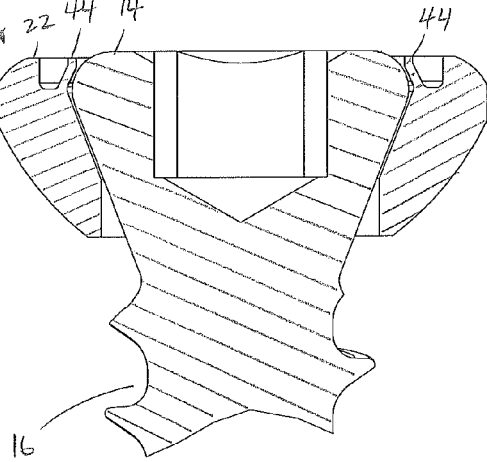

us 8,585,743 B2

LOW PROFILE SCREW AND WASHER SYSTEM FOR BONE PLATING

BACKGROUND OF THE INVENTION

1. Field of the Invention

This invention relates broadly to surgery. More particularly, this invention relates to orthopedic fasteners.

2. State of the Art

According to recent trends, there is a need to reduce the profile of bone plates and screws for internal fixation of fractured bones. This is especially important for plates used to repair fractures of the elbow, which has relatively little protection by overlying soft tissues and is highly vulnerable, for example, to accidental bumping as the fracture heals. Development of very thin, anatomically conforming bone plates has created new challenges related to plate-to-bone attachment. More specifically, improved designs for fastener systems are needed so that minimal implanted hardware protrudes undesirably above the top surface of the plate and irritates and/or inflames the overlying tissues.

In general, there is also a need to reduce the inventory of bone screws required for internal fixation procedures due to the high cost of providing and maintaining a sterilizable surgical kit containing a large quantity of different screw sizes and types for the varied patient anatomies and fracture types.

There have been developed bone screws and retainable (or captive) washers that attach to the screw head. However, the focus on such prior systems apparently was not to provide a low profile screw and washer assembly for use on bone plates that are thinner than previous, conventional bone plates. Nor was emphasis placed on providing a bone screw that may be used for multiple functions, thereby reducing the required inventory of screws required for a surgical procedure.

SUMMARY OF THE INVENTION

A low profile bone screw system includes a retainable washer and a low profile bone screw having a head for insertion into the washer. The washer has an axial bore for receiving the screw head. In accord with one preferred aspect of the invention, the maximum diameter of the washer is located above the vertical center of the washer. The lower surface of the washer is smoothly curving from the lowest portion to the portion of maximum diameter, and preferably provided with a radius of curvature. These features allow the washer to seat low in a plate hole to minimize protrusion of the washer and screw head above the plate.

In accord with another aspect of the invention, various means are provided for engaging the washer relative to the screw head to lock the two components together. According to several embodiments, the washer is adapted to engage a non-threaded conical screw head. For such screws, the means for engaging the washer relative to the screw includes at least one interference element extending radially inward from the axial bore on the washer. The at least one interference element may be resiliently or plastically deformable. When a user inserts the screw into the washer and the screw head is fully seated in the washer, either one or both of the interference element and the head of the screw deforms, such that the screw and washer are sufficiently joined together to be handled as a unit during the surgical procedure. According to another embodiment, the washer is adapted to engage a threaded screw head. In such embodiment, the engagement means is a threaded axial bore. The washer preferably includes a recess at its upper end in order to receive the screw head in a low profile manner.

According to another aspect of the invention, dispensers are provided including one or more stores of washers in the dispensers. The dispensers are preferably operably associated with a sterilizable surgical tray also containing a plurality of low profile orthopedic screws, additional orthopedic implants and/or orthopedic instruments.

Additional advantages of the invention will become apparent to those skilled in the art upon reference to the detailed description taken in conjunction with the provided figures.

BRIEF DESCRIPTION OF THE DRAWINGS

FIG. 1 is a perspective view of an assembly of a bone screw and washer according to a first embodiment of the invention.

FIG. 2 is a perspective view of a washer according to the first embodiment of the invention.

FIG. 3 is a section view of the washer of FIG. 2.

FIG. 4 is a section view similar to FIG. 2 showing the assembly of the bone screw to the washer.

DETAILED DESCRIPTION OF THE PREFERRED EMBODIMENTS

Figure 6:
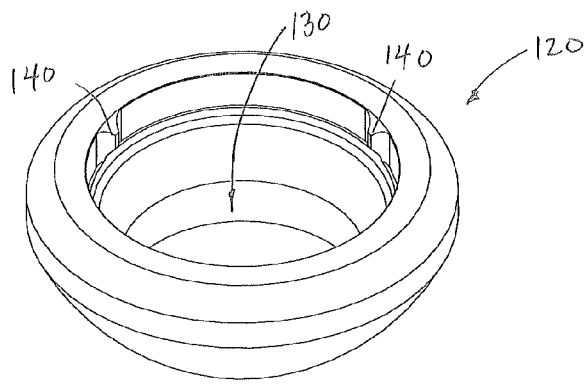
FIG. 6 is a perspective view of a washer according to the second embodiment of the invention.

Referring to FIGS. 1 through 4, an embodiment of a low profile bone screw system 10 is shown. The system 10 includes a low profile bone screw 12 having a conical head 14 (seen best in FIG. 4) with a driver engaging slot 15, and shaft 16 with bone engaging threads 18. Such a low profile conical head screw 12 may be inserted into a threaded, locking hole in an orthopedic plate (without threaded engagement therein) or assembled with a washer 20 retained on the head 14 of the screw for use in a dynamic compression slot of an orthopedic plate.

The washer 20 has a top 22, a bottom 24, and a maximum vertical dimension V between the top 22 and bottom 24 that defines a vertical center C at a midpoint of the maximum vertical dimension. A smoothly curving lower surface 26 extends from the bottom 24 to the circumference 28 of the washer at the maximum diameter D of the washer, which occurs above the vertical center C. More preferably, the maximum diameter D is located approximately two-thirds up from the bottom 24 of the washer 20. These features allow the washer to seat low in a plate hole to minimize protrusion of the washer 20 and screw head 14 above a plate so as to reduce tissue irritation/inflammation and minimize patient discomfort.

An axial bore 30 extends through the washer 20 and has an upper conical portion 32 and a lower cylindrical portion 34. The upper conical portion 32 is defined by a bore surface 36 inclined by 22°±3° relative to the bore axis A. The bore 30 includes means for engaging the head 14 of the screw 12 to the washer 20 such that the screw 12 and washer 20 are assembled to each other to be handled together as a unit during a surgical procedure. According to a first embodiment, a circumferential ridge 38 is provided within the axial bore 30. Retaining tabs 40 are circumferentially displaced along the ridge 38 and directed radially inwardly into the bore 30. The tabs 40 have a first portion 42 angled at 25°±3° relative to the bore axis A, and a free end 44 parallel to the bore axis A. The free ends 44 are substantially co-planar with the top 22 of the washer 20 (FIG. 4). Preferably six tabs 40 are provided, with each tab extending 5°±3° about the circumference of the ridge 38 (FIG. 2). A channel 46 is defined between the tabs and the bore (FIGS. 2 and 3).

As the screw head 14 is forced through the washer 20 during assembly, the head 14 deflects the tabs 40 radially outward to provide sufficient access for the head to be received with the conical portion 32 of the bore 30, and the tabs 40 then snap back over the head 14 to lock the head relative to the washer 20. The head 14 and conical portion 32 have a common inclination permitting a stable assembly. The angled first portion 42 of each tab 40 is configured to seat against a convex top surface of the head 14 of the screw. In addition, by having the free end 44 of the tab 40 terminate even with the top 22, the contour profile at the top of the assembly has an increased smoothness to reduce any potential irritation.

Turning now to FIGS. 5 through 9, according to another embodiment, a washer 120 preferably having the same outer shape as washer 20 described above is provided with different means for engaging the same screw 12. In general, the means includes a structure provided within an upper portion of the bore that either (i) plastically deforms upon contact with the washer, or (ii) causes plastic deformation of the washer, or (iii) causes a combination thereof, as the screw head 14 is forced within the axial bore 130 of the washer 120 upon assembly of the washer relative to the screw head. More particularly, the axial bore 130 of the washer 120 includes a central conical portion 132, a lower cylindrical portion 134, and an upper cylindrical portion 135. The upper cylindrical portion 135 is provided with a plurality of evenly spaced interference elements 140 (proximate the top of the washer) that radially extend into the upper cylindrical portion 135 to define a diameter smaller than the diameter of the screw head 14 that seats in the corresponding portion of the bore.

The screw 12 and washer 120 may be formed from stainless steel, titanium, titanium alloy, cobalt chrome, or a polymer. In addition, the screw 12 and washer 120 may be formed from the same material to allow a cold formed weld assembly. The screw 12 and washer 120 may alternatively be formed from dissimilar materials of different hardnesses, depending on the desired deformation of interference elements 140 and the screw head 14. The washer 120 may be constructed of a softer material than the screw head 14 to facilitate deformation of the interference elements 140 by the screw head 14, or the washer 120 (or at least the interference elements 140 thereof) may be formed of a harder material than the screw head 14 to facilitate deformation of the screw head by the interference elements 140.

Figure 5:
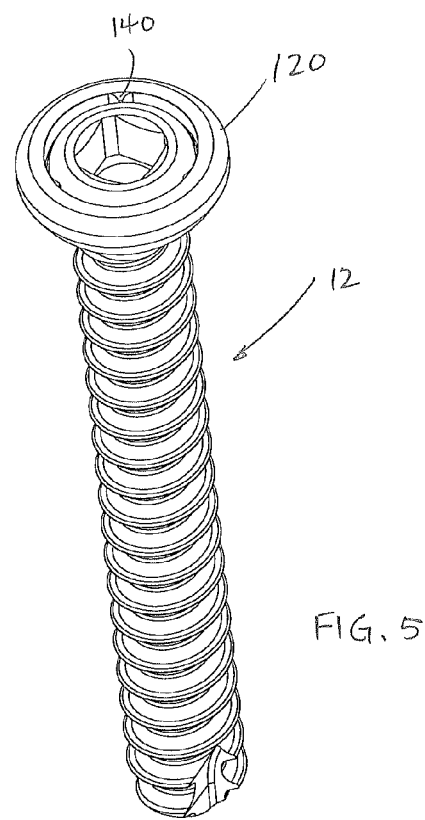
FIG. 5 is a perspective view of an assembly of a bone screw and washer according to a second embodiment of the invention.
Figure 7:
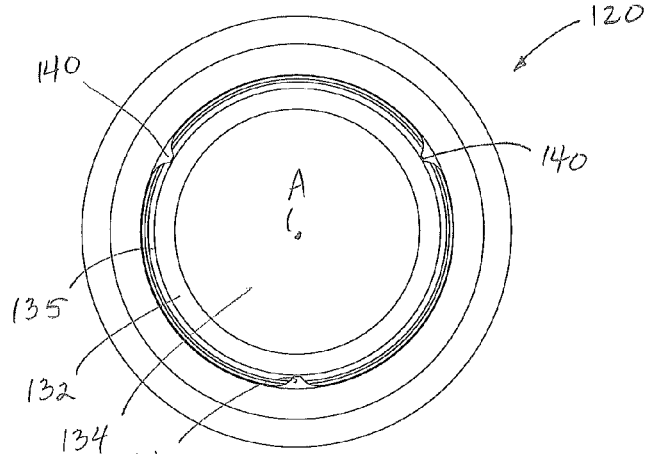
FIG. 7 is a top view of the washer of FIG. 6.
Figure 8:
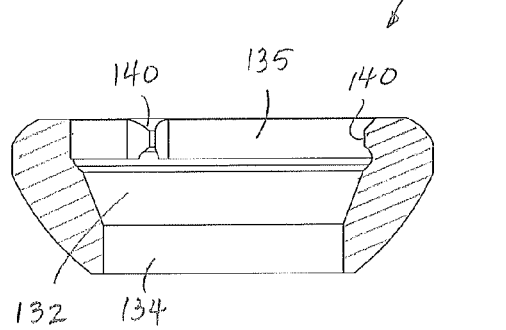
FIG. 8 is a section view of the washer of FIG. 6.
Figure 9:
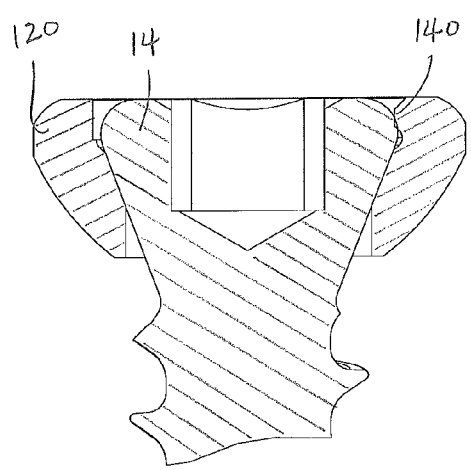
FIG. 9 is a section view similar to FIG. 8 showing the assembly of the bone screw to the washer.
Figure 11:
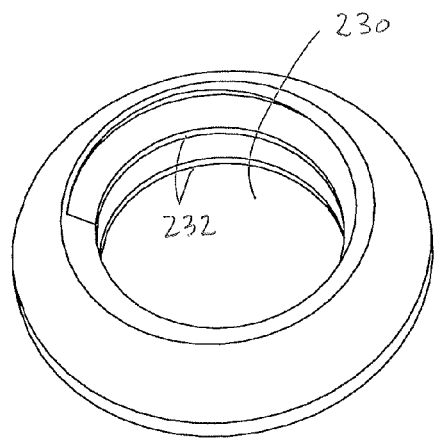
FIG. 11 is a perspective view of a washer according to the third embodiment of the invention.
Figure 12:
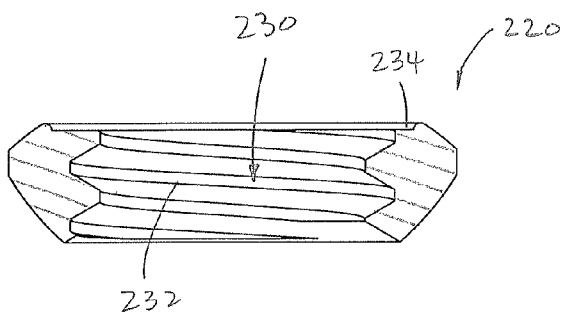
FIG. 12 is a section view of the washer of FIG. 11.
Figure 10:
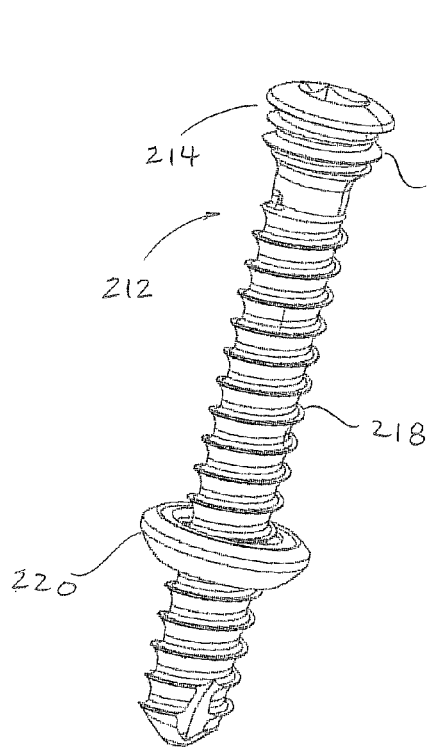
FIG. 10 is a perspective view of a partial assembly of a bone screw and washer according to a third embodiment of the invention.

When a user forces the screw 12 into the washer 120 and the screw head 14 fully seats in the washer, either one or both of the interference elements 140 and the head 14 of the screw 12 deforms. The resulting assembly, as seen in FIGS. 5 and 9, is sufficiently joined together to be handled as a unit during the surgical procedure.

Figure 13:
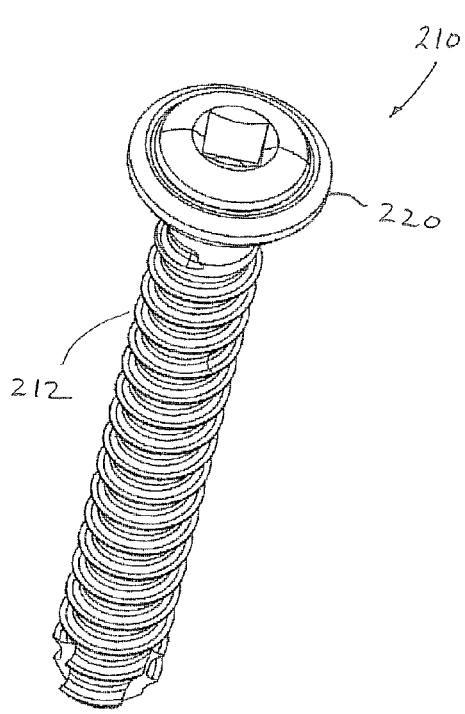
FIG. 13 is an end perspective view of the bone screw and washer assembly according to the third embodiment of the invention.

Referring now to FIGS. 10 through 13, according to yet another embodiment, the system 210 includes a screw 212 with a cylindrical head 214 having a machine thread 216 thereabout and a threaded shaft 218. The screw 212 is normally used for fixed angle coupling relative to a plate with a mating threaded hole. The system also includes a washer 220, which preferably has substantially the same external shape as the previously described washers. The washer 220 defines an axial cylindrical bore 230 having an internal helical thread 232. The screw head 214 stably threads into engagement with the thread 232 in the washer bore 230. The washer 220 preferably includes a recess 234 at its upper end in order to receive and recess the screw head 214 in a low profile manner. When the screw 214 and washer 220 are assembled, the screw 214 is converted from a fixed angle locking screw to a lagging screw (FIG. 13).

Figures 14, 15:
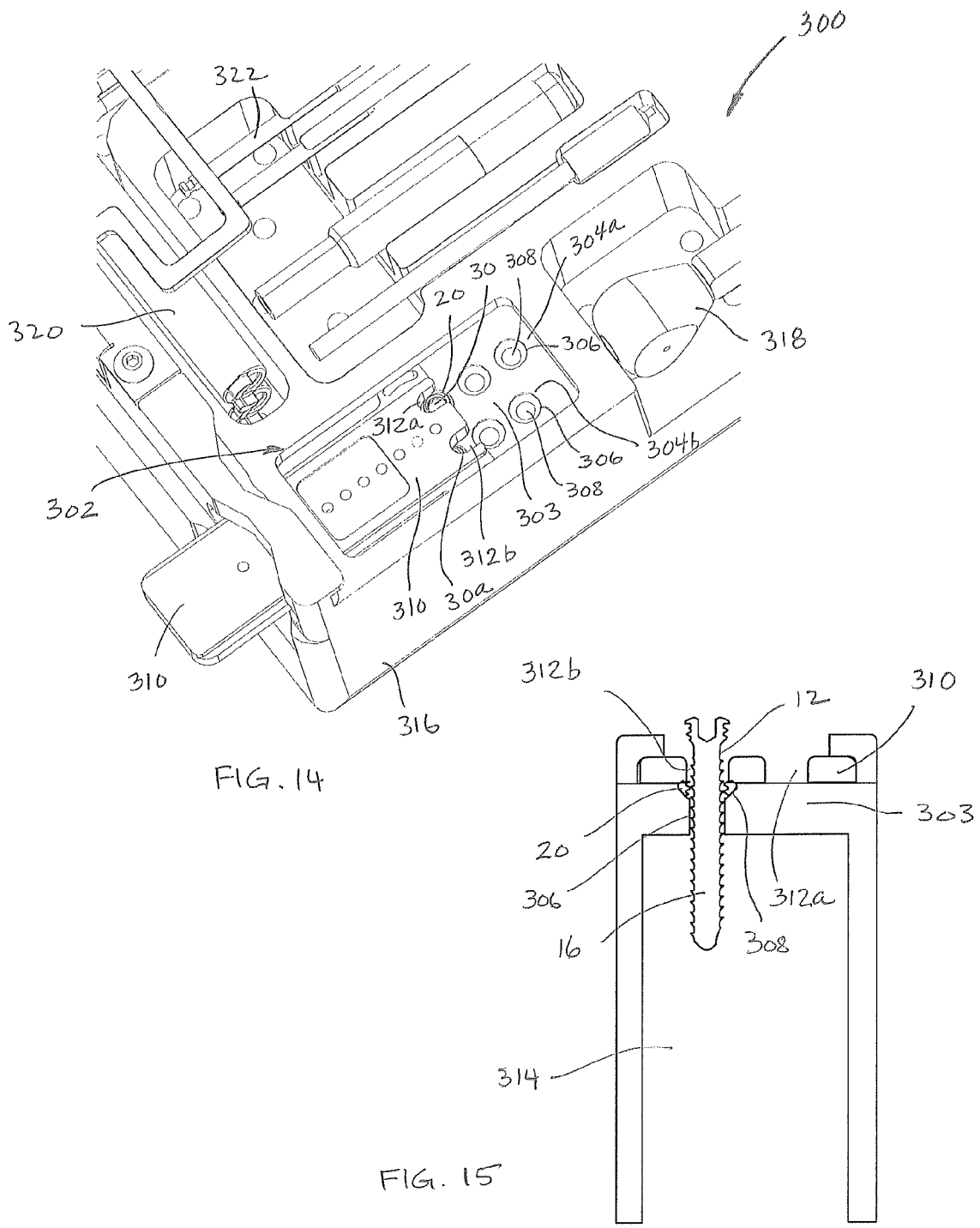
FIG. 14 is a broken perspective view of surgical kit including a first embodiment of a washer dispenser according to the invention.
FIG. 15 is a schematic view of the washer dispenser according to the invention.
Figure 17:
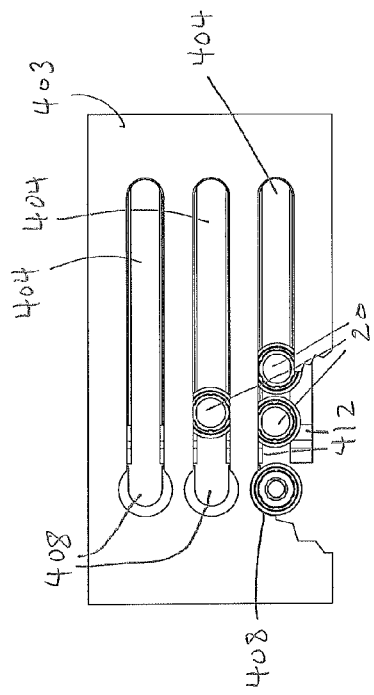
FIG. 17 is a broken top view of the second embodiment of a washer dispenser according to the invention.
Figure 18:
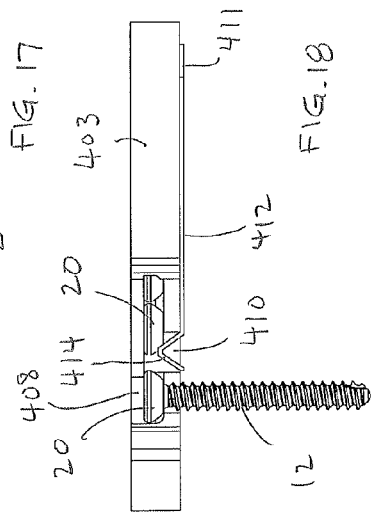
FIG. 18 is a side elevation of the second embodiment of a washer dispenser according to the invention.
Figure 19:
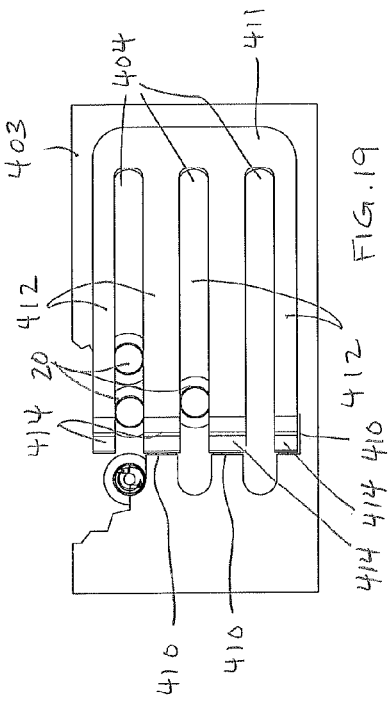
FIG. 19 is a broken bottom view of the second embodiment of a washer dispenser according to the invention.
Figure 16:
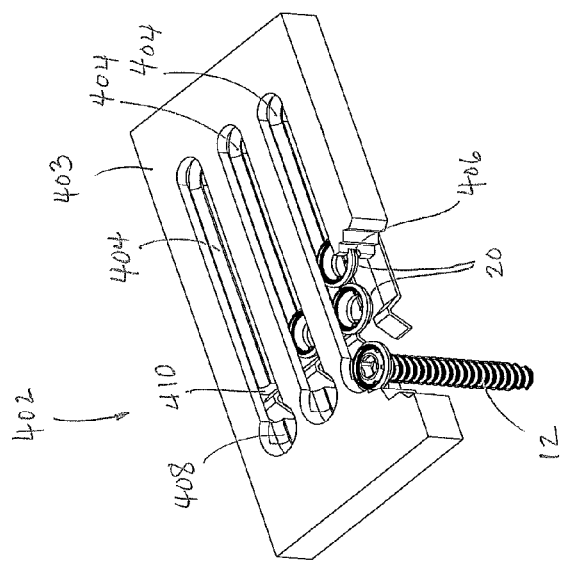
FIG. 16 is broken perspective view of a second embodiment of a washer dispenser according to the invention.

Referring now to FIGS. 14 and 15, according to another aspect of the invention, a first kit 300 is provided for dispensing and facilitating assembly of any of the washers 20 (120, 220) described herein with screws in accord with the invention. The kit includes a dispenser 302 having a store of washers 20 on a tray 303 or other carrier. More particularly, the tray 303 has two longitudinally offset rows 304a, 304b of recesses 306 with central holes 308 therein in communication with a lower cavity 314 (FIG. 15). The washers are received in the recesses 306 with the axial bores 30 of the washers centered over the central holes 308. A lid 310 is coupled relative to the tray 303 to retain the washers therein. The lid 310 preferably indexes in a slidable manner relative to the store to controllably expose the axial bore of one washer 20 at a time. The lid 310 is shaped to define two cutouts 312a, 312b which alternately align relative to the axial bores 30 of the washers 20 in the alternate rows 304a, 304b as the lid 310 is indexed from one predetermined location to the next. As the lid 310 is indexed to expose an axial bore of a washer, the area surrounding the respective cutouts, e.g., cutout 312a, allows the lid 310 to provide contact against the periphery of a washer 30 to stabilize the washer while its axial bore 20 is exposed. Such stabilization allows axial and/or rotational forces to be applied by a screw 12 (FIG. 15) to the washer 30 during assembly of the screw to the washer. The screw shaft is received in the cavity 314 during assembly. Once the screw 12 is assembled to the washer 20, the lid 310 is indexed another step to release the assembled screw and washer from the dispenser 302 and expose the axial bore of a next washer 30a.

The dispenser 302 may accept replaceable cartridges of washers. The dispenser 302 is preferably operably associated with a sterilizable surgical tray 316 also containing a plurality of low profile orthopedic screws 12, additional orthopedic implants such as plates for placement on the diaphysis or metaphysis of long bones, and/or orthopedic instruments for implanting such implants including, e.g., rotational drivers 318 for the screws, plate benders 320 for shaping orthopedic plates, and drill bits 322 for drilling holes into bone to accept orthopedic fasteners such as screw 12.

Turning now to FIGS. 16 through 19, a second dispenser 402 for a kit is provided for dispensing and facilitating assembly of any of the washers 20 (120, 220) described herein with screws in accord with the invention. The dispenser 402 has a store of washers 20 on a carrier 403. The carrier 403 defines at least one, and preferably a plurality of, elongate keyhole slots 404 defining lateral grooves 406 in which the peripheries of the washers 20 are received and supported. Screws 12 can be inserted through the supported washers 20 and forced into engagement therein, as described above. An enlarged generally circular opening 408 through which the washers 20 can be individually loaded into the slot 404 and removed therefrom is provided at an end of each slot 404. The lower portion of the carrier has a recess 410 adjacent each enlarged opening 408. A sheet 411 has an end fixed relative to the lower surface of the carrier 403. The sheet 411 defines leaf springs 412 that extend from the fixed end along both sides of each of the slots 404. The leaf springs 412 each have a retainer 414 that enters a respective recess 410. The retainers 414 inhibit release of washers 20 through the enlarged openings 408 unless sufficient manual force is applied to a washer 20 to resiliently deform a respective leaf spring 412 to permit passage of a washer 20 from the slot 404 into the adjacent enlarged opening 408, particularly once the washer 20 is assembled with the screw 12 so that the screw and washer are engaged together so as to be handled as a unit. The carrier 403 may be coupled to or incorporated into a surgical kit, and may be in the form of a cartridge that is removable and replaceable within a surgical kit.

The versatility of using a single bone screw in either a locking screw hole or with a retainable washer in an elongated hole of a bone plate reduces the quantity of screws that must be available during the surgical procedure. This potentially reduces the overall cost of the surgical kit because it is much less expensive to make retainable washers than to make bone screws.

There have been described and illustrated herein several embodiments of a washers for screws, screw and washer assemblies, and kits for dispensing washers during a surgical procedure. While particular embodiments of the invention have been described, it is not intended that the invention be limited thereto, as it is intended that the invention be as broad in scope as the art will allow and that the specification be read likewise. Thus, while materials have been disclosed with respect to particularly embodiments, it will be appreciated that such materials can be used with respect to all embodiment of the invention. It will therefore be appreciated by those skilled in the art that yet other modifications could be made to the provided invention without deviating from its spirit and scope as claimed.

What is claimed is:

1. A screw and washer system, comprising:
a) a screw having a non-threaded conical head and a shaft with bone engaging threads, said head of said screw provided with a distal end from which said shaft extends, and a proximal end opposite said shaft, said proximal end defining a convex top surface portion and a torque driver engagement portion; and
b) a washer having a top, a bottom, a maximum vertical dimension extending between the top and bottom, a vertical center at a midpoint of said maximum vertical dimension, a maximum diameter provided above said vertical center, a smoothly curving exterior lower surface extending upward to said maximum diameter, an axial bore extending through said washer from said top to said bottom, said bore having an upper conical portion shaped to receive in mating contact the conical head and a lower cylindrical portion, and at least one interference element extending radially inward into said axial bore of the washer only above said upper smooth conical portion so that when said head of said screw is inserted into said axial bore of said washer with said conical head in mating contact against said conical portion of said bore, said at least one interference element extends above said conical portion and into contact about said convex top surface portion to retain said screw and washer as an assembly.

2. A screw and washer system according to claim 1, wherein:
said at least one interference element is resiliently deformable.

3. A screw and washer system according to claim 2, wherein: said at least one interference element is a resiliently deformable tab having a free end that terminates coextensively with said top of said washer.

4. A screw and washer system according to claim 3, wherein: said axial bore includes a longitudinal axis, and said free end is oriented parallel to said longitudinal axis.

5. A screw and washer system according to claim 2, wherein:
said washer defines a ridge recessed below said top within said axial bore, and said at least one interference element extends from said ridge.

6. A screw and washer system according to claim 2, wherein:
said screw and washer are assembled in a snap-fit engagement.

7. A screw and washer system according to claim 1, wherein: when said screw is inserted into said washer and said head is fully seated in said axial bore of said washer, either one or both of said at least one interference element and the head of said screw deforms, such that the screw and washer are sufficiently joined together to be handled as a unit during a surgical procedure.

8. A screw and washer system according to claim 7, wherein:
said at least one interference element is plastically deformable upon engagement with said head of said screw.

9. A screw and washer system according to claim 7, wherein:
said head of said screw deforms upon engagement with said at least one interference element.

10. A screw and washer system according to claim 7, wherein:
said washer and screw head have a same hardness, and engagement of said at least one interference element with said head of said screw provides a cold formed weld assembly.

11. A screw and washer system according to claim 7, wherein:
said screw and washer are formed from dissimilar metals.

12. A screw and washer system according to claim 1, wherein:
said washer has a planar uppermost surface.

13. A screw and washer system according to claim 1, wherein:
said screw and washer are assembled in a cold formed weld assembly.

14. A screw and washer system according to claim 1, wherein:
said smoothly curving exterior lower surface of said washer extends upward from said bottom to said maximum diameter.

15. A screw and washer system, comprising:
a) a screw having a head and shaft, said head defining a non-threaded conical exterior shape and having a proximal end defining a convex top surface portion and a torque driver engagement portion, and said shaft provided with bone engaging threads; and
b) a washer having a top, a bottom, a maximum vertical dimension extending between the top and bottom, a vertical center at a midpoint of said maximum vertical dimension, a maximum diameter provided above said vertical center, a smoothly curving exterior lower surface extending upward to said maximum diameter, an axial bore extending through said washer from said top to said bottom, said bore having an upper conical portion shaped to receive in mating contact the conical exterior shape and a lower cylindrical portion, and at least one interference element extending radially inward into said axial bore of the washer only above said upper conical portion so that when said head of said screw is inserted into said axial bore of said washer with said conical exterior shape of said head is in mating contact against said conical portion of said bore, said at least one interference element extends above said conical exterior shape of said head and into contact with said convex top surface portion to retain said screw and washer as an assembly, wherein in said assembly said top surface of said washer and said proximal end of said head of said screw are substantially vertically aligned.

16. A screw and washer assembly according to claim 15, wherein: the entirety of said screw head is non-threaded.

* * * * *

UNITED STATES PATENT AND TRADEMARK OFFICE
CERTIFICATE OF CORRECTION

| | | |
|---|---|---|
| PATENT NO. | : 8,585,743 B2 | Page 1 of 1 |
| APPLICATION NO. | : 12/210627 | |
| DATED | : November 19, 2013 | |
| INVENTOR(S) | : Ampuero et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1116 days.

Signed and Sealed this
Eighteenth Day of August, 2015

Michelle K. Lee
*Director of the United States Patent and Trademark Office*